United States Patent [19]

Sawhill

[11] Patent Number: 5,146,929

[45] Date of Patent: Sep. 15, 1992

[54] LUMBAR SPINE MOTION SENSOR

[76] Inventor: James A. Sawhill, P.O. Box 115, Lyndon Center, Vt. 05850

[21] Appl. No.: 776,061

[22] Filed: Oct. 11, 1991

[51] Int. Cl.⁵ .............................................. A61B 5/103
[52] U.S. Cl. .................................................... 128/781
[58] Field of Search ........................ 128/774, 781, 782; 33/511, 512

[56] References Cited

U.S. PATENT DOCUMENTS

| | | | |
|---|---|---|---|
| 4,108,164 | 8/1978 | Hall, Sr. | 128/25 |
| 4,306,571 | 12/1981 | McLeod, Jr. | 128/782 |
| 4,436,099 | 3/1984 | Raftopoulos | 128/782 |
| 4,665,928 | 5/1987 | Linial et al. | 128/782 |
| 4,667,685 | 5/1987 | Fine | 128/782 |
| 4,800,897 | 1/1989 | Nilsson | 128/782 |
| 4,804,001 | 2/1989 | McLeod, Jr. | 128/782 |
| 4,834,057 | 5/1989 | McLeod, Jr. | 128/782 |
| 4,882,677 | 11/1989 | Curran | 364/413 |
| 4,883,069 | 11/1989 | McLeod | 128/782 |
| 4,893,808 | 1/1990 | McIntyre et al. | 272/94 |
| 5,012,819 | 5/1991 | Marras et al. | 128/781 |
| 5,094,249 | 3/1992 | Marras et al. | 128/781 |

FOREIGN PATENT DOCUMENTS

WO90/00879  2/1990  Int'l Pat. Institute .
596235  9/1976  U.S.S.R. .

OTHER PUBLICATIONS

Isostation B-200 advertisement, (Nov. 1989).
Motion Analysis Corporation advertisement (Nov. 1989).
Cybex Back Systems advertisement, (Nov. 1989).
Dynatron 360, (Sep. 1989).
Kettelkamp, Donald B., et al., "An Electrogoniometric Study of Knee Motion in Normal Gait," *The Journal of Bone and Joint Surgery*, vol. 52-A, No. 4, Jun. (1970) 775-790.
Chao, Edmund Y. S. and Hoffman, Ross R., "Instrumented Measurement of Human Joint Motion," *ISA Transactions*, vol. 17, No. 1, (1978) 13-19.
Foster, David L. et al., "Telemetry Instrumentation for Kinesiologic Studies of Knee Motion," *Medical Research Engineering*, vol. 13, No. 2, Apr. (1980), 17-21.
Townsend, M. A. et al., "Total Motion Knee Goniometry," *Journal of Biomechanics*, (1977) vol. 10, No. 3, 183-193.
Chao, E. Y. et al., "Electrogoniometer for the Measurement of Human Elbow Joint Rotation," *Journal of Biomechanical Engineering* (Nov. 1980), vol. 102, 301-310.
"Wrist and Shoulder Motion Analyzer," Research Disclosure 21119, (Nov. 1981) No. 211.

*Primary Examiner*—Max Hindenburg
*Attorney, Agent, or Firm*—Wells, St. John, Roberts, Gregory & Matkin

[57] ABSTRACT

A portable instrument for measuring bodily movement in the lumbar spinal area includes an articulated enclosure having a first housing fastened to the body of a subject by means of a first rigid plate. A hinged second housing is movably connected to a second plate. Both the first and second plates are adapted to be fixed behind the body of a subject with the second plated at a location vertically above the first plate. Transducers or sensors within the housings are used to measure hinged motion between the two housings, as well as relative transverse bending movement and torsional movement between the two plates. These relative movements produce electrical signals that directly correspond to the amount of flexion/extension, lateral bending and axial rotation occurring at the lumbar spine of a monitored subject.

7 Claims, 6 Drawing Sheets

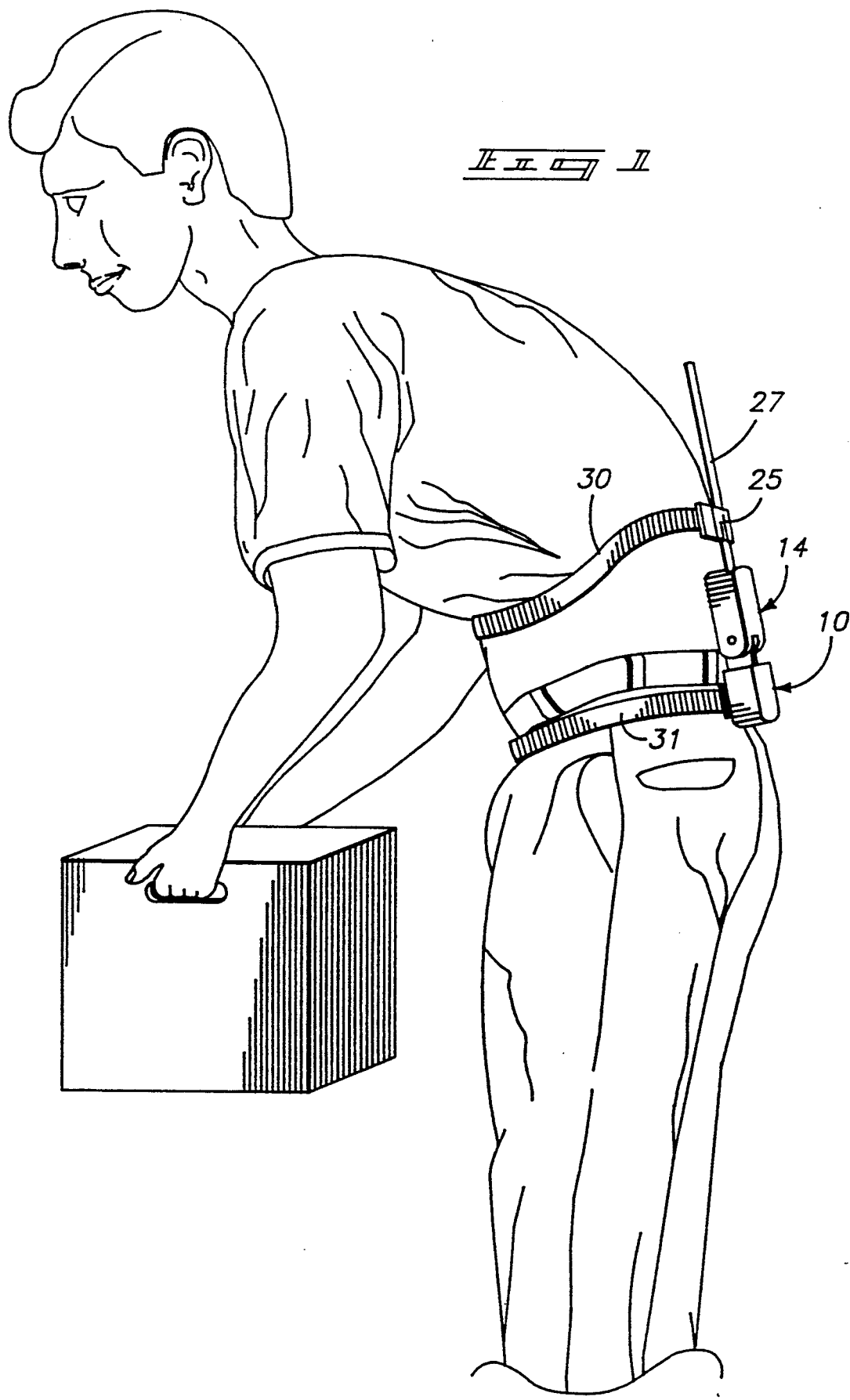

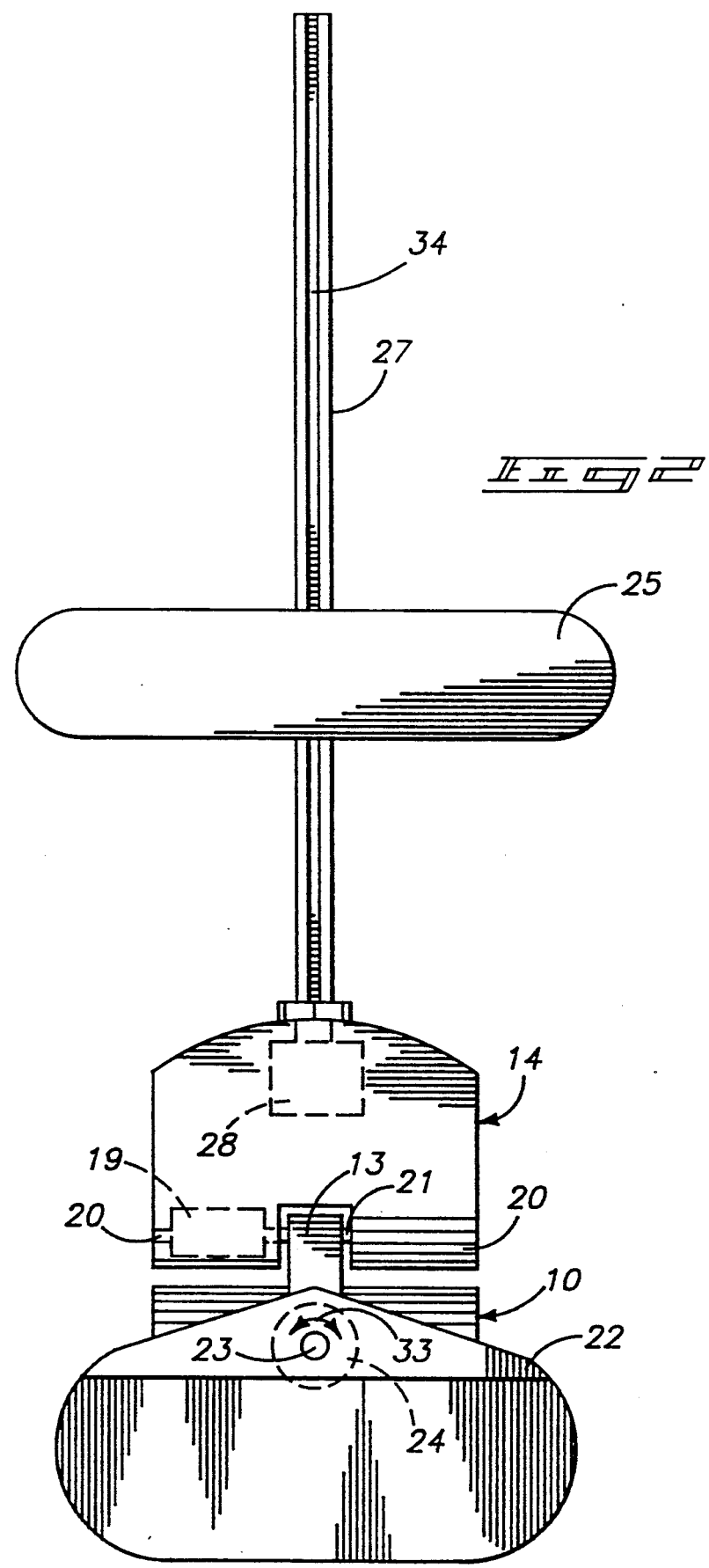

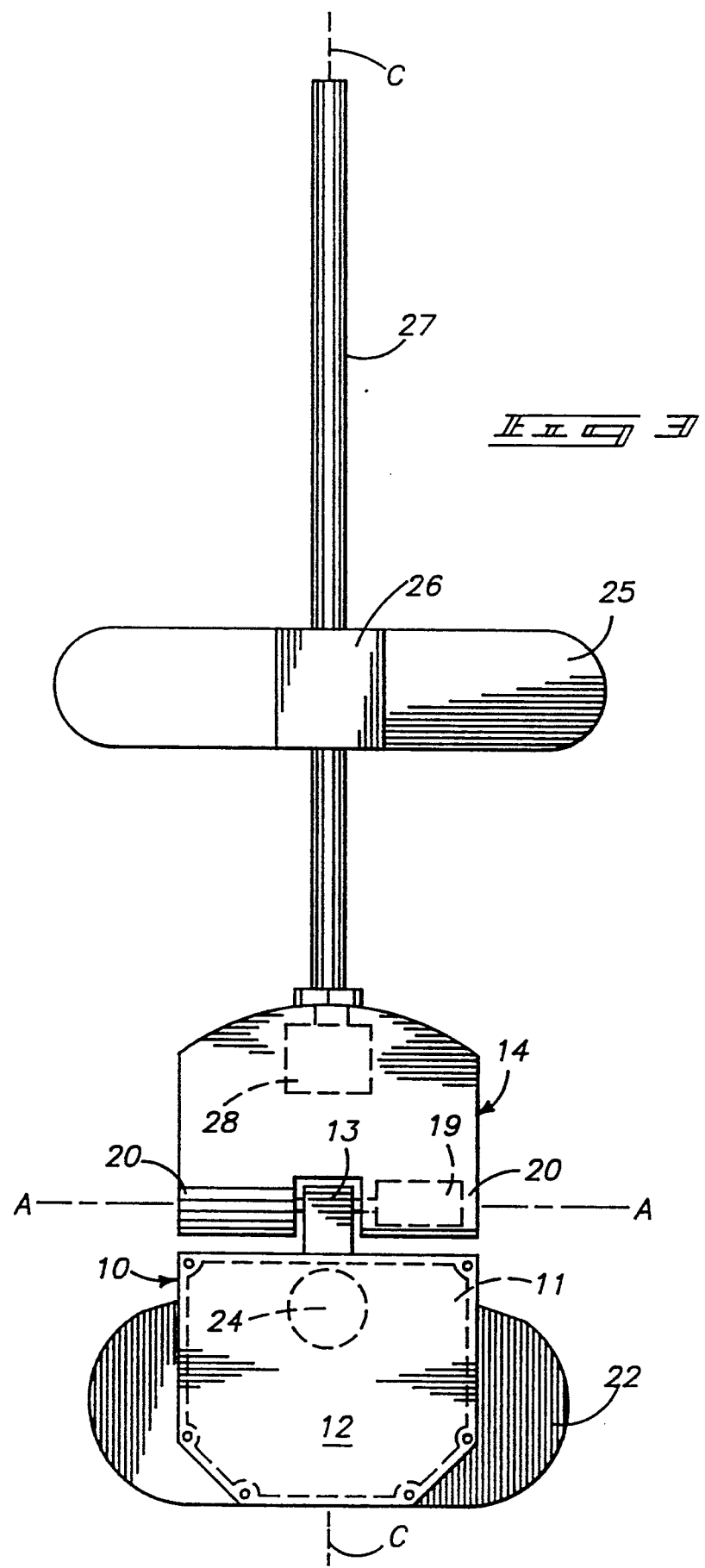

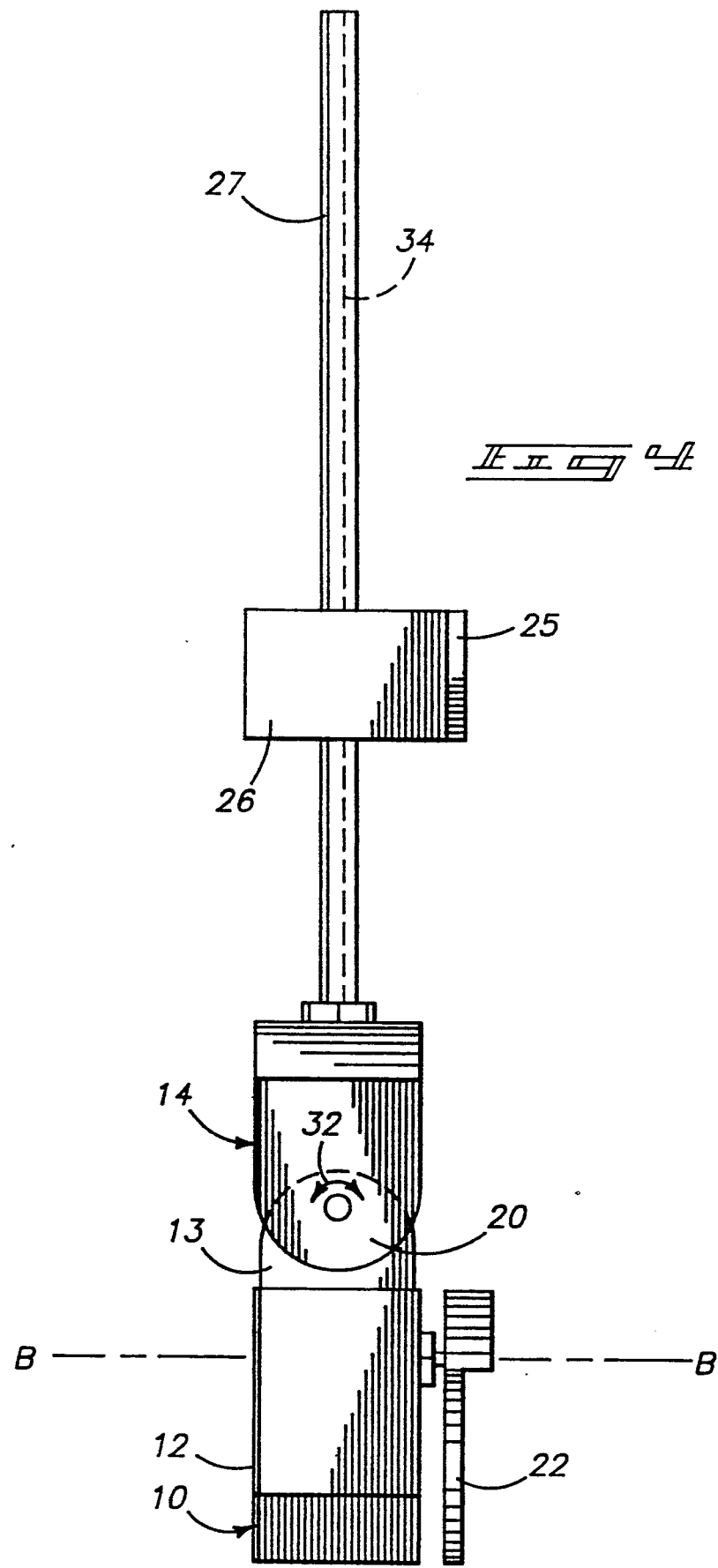

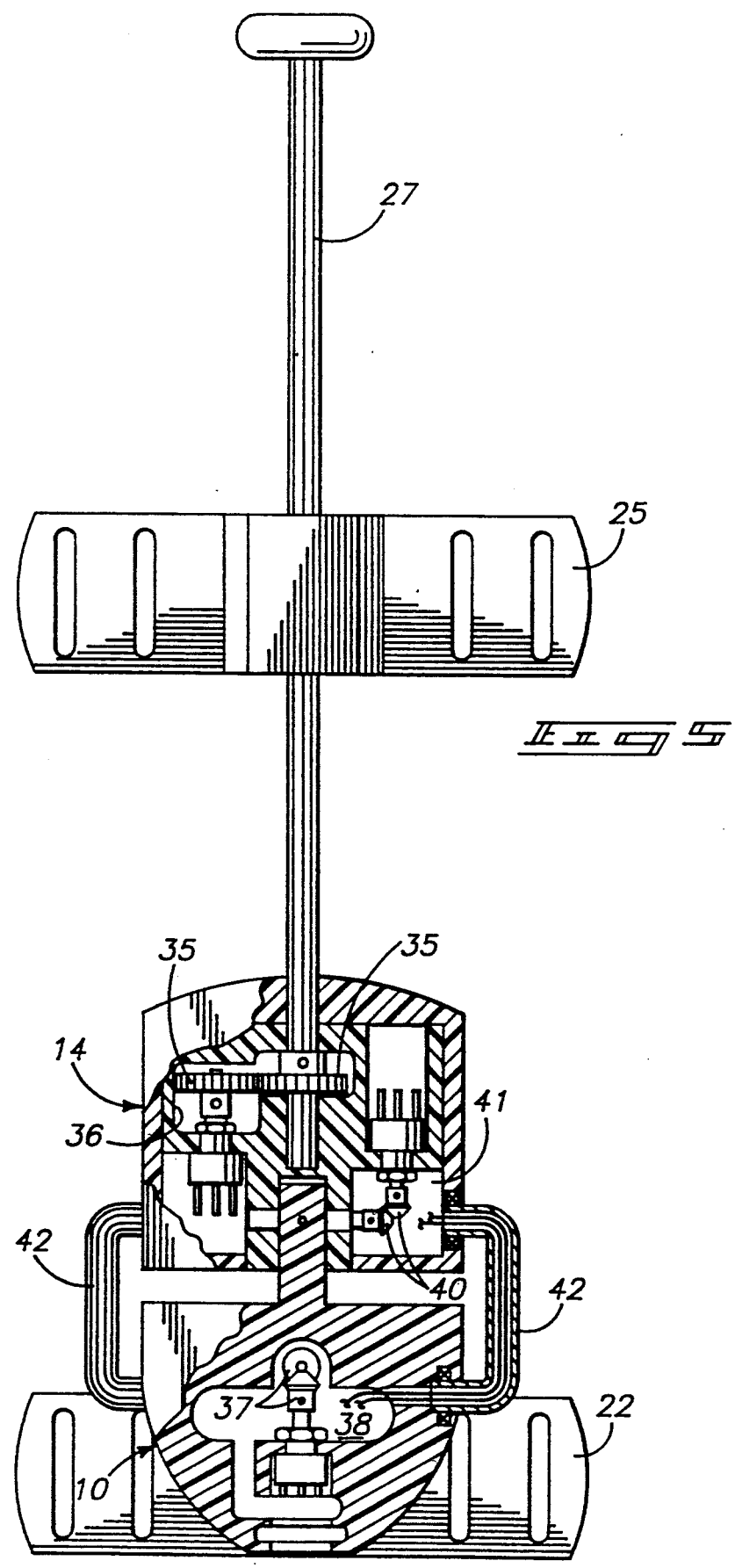

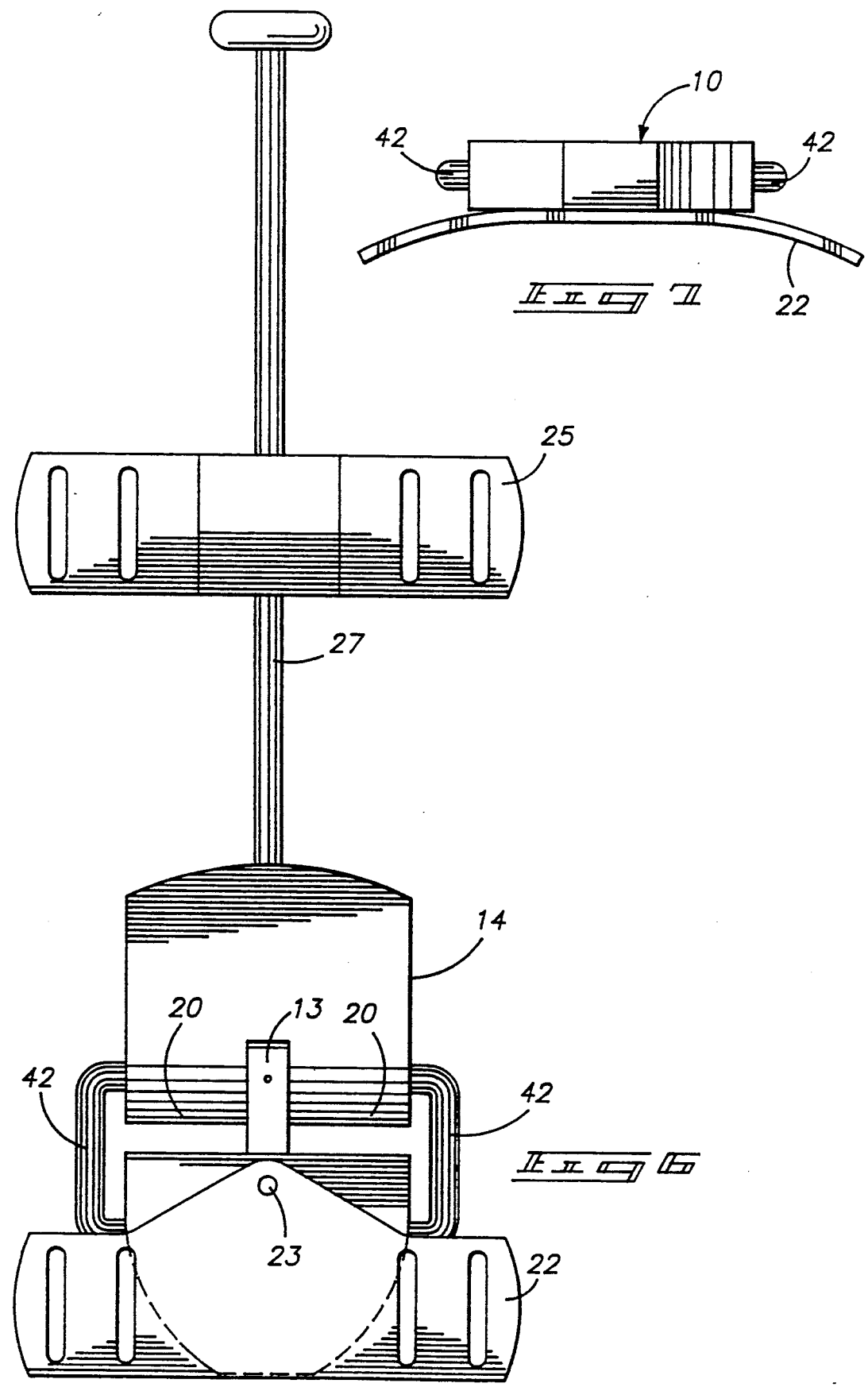

LUMBAR SPINE MOTION SENSOR

TECHNICAL FIELD

This disclosure pertains to portable devices that can be attached to the body of a person for empirically measuring movement of the lumbar region of the subject's spine. It provides the user with accurate measurements of three separate degrees of rotation in the low back area.

BACKGROUND OF THE INVENTION

Quantitative measurement of spinal motion in the lower back or lumbar region is vital in evaluating and treating physical impairment in this area, whether due to trauma, degenerative disease, or other causes, Because small inaccessible spinal joint do not readily lend themselves to the external visual observations typically required by standard goniometric measurement processes, such techniques for measuring spinal movement have been recognized to be highly inaccurate.

The mobility of spinal segments is confounded by motion above and below the points of measurement. The complexities involved in measuring spinal movement in the lumbar region have led to the development of large and cumbersome apparatus which are not only expensive, but substantially reduce the ability of a subject to move normally during their use.

The present device was designed to provide an accurate system for measuring the range of motion in the lumbar spinal region without use of visual techniques or cumbersome physical equipment that limits the activities of the subject. It is applicable to screening of employees to evaluate range-of-motion in all three planes of low back movement. It is also useful for evaluation of injuries, providing reproducible results that can serve as a measure of damage suffered. It also has application to period evaluation of the effects of back rehabilitation programs.

The miniature measurement instrument disclosed in detail below permits the user to perform effective three dimensional back testing and rehabilitation conveniently. Its portable operation, fast set-up, accuracy and reliability allow it to be used more efficiently and effectively than prior large-scale testing systems. Electrical or electronic measurements can be recorded to provide real-time displays for range of motion studies, biofeedback purposes and motion analysis.

BRIEF DESCRIPTION OF THE DRAWINGS

Preferred embodiments of the invention are described below with reference to the accompanying drawings, which are briefly described below.

FIG. 1 is a perspective view illustrating use of the present device;

FIG. 2 is a front elevation view of the assembled device;

FIG. 3 is a back elevation view;

FIG. 4 is a side elevation view;

FIG. 5 is a back view of a preferred embodiment of the device;

FIG. 6 is a front elevation view;

FIG. 7 is a bottom view.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

FIGS. 1-4 illustrate the basic elements of the present device, which is designed for measuring angular rotations of the lumbar spine about three axes. FIGS. 5-7 illustrate a more refined embodiment of the device, which is the best mode contemplated at present.

The disclosed instrument is designed to be readily strapped to a subject, in the manner generally illustrated in FIG. 1. Upper and lower straps 30, 31 encircle the body of the subject. They mount the device immediately adjacent to the lumbar spine that is being monitored. The body of the subject, whether clothed or unclothed, is frictionally engaged by two plates 22 and 25 fixed respectively to the straps 31 and 30. Relative movement between the two plates 22 and 25, due to spinal movement, is detected by appropriate transducers within the device. The transducers or motion sensors produce signals representative of the amounts of motion occurring about three perpendicular axes that are accurately located relative to the subject's spine.

Most of the components of the device are located within an articulating enclosure that includes a first housing 10 and a second housing 14.

A first pivot connection joins the two housings 10, 14 for relative motion about a first axis denoted by line A—A in FIG. 3. Pivotal movement of the housings 10, 14 about the first axis, which is illustrated by arrows 32 in FIG. 4, will correspond to flexion/extension of the lumbar spine of the subject.

A second pivot connection mounts plate 22 to the first housing 10 about a second axis, illustrated by line B—B in FIG. 4. The second axis (line B—B) is perpendicular to the first axis (line A—A). In the illustrated embodiments, the second axis is also spaced distally from the first axis, but they can intersect as well. Relative pivotal movement between plate 22 and the first housing 10, which is illustrated by arrows 33 in FIG. 2, will correspond to lateral bending of the subject's lumbar spine.

A third pivot connection is provided between plate 25 and the second housing 14 about a third axis, shown as line C—C in FIG. 3. The third axis (line C—C) is perpendicular to and intersects both the first axis (line A—A) and the second axis (line B—B). Relative pivotal movement between plate 25 and second housing 14 about the third axis will correspond to axial rotation of the subject's lumbar spine.

A plurality of sensors are included within the articulating enclosure for separately measuring relative pivotal motion between the first and second housings 10, 14 about the first axis (line A—A), as well as relative pivotal motion between the plate 22 and first housing 10 about the second axis (line B—B) and relative pivotal motion between the plate 25 and the second housing 14 about the third axis (line C—C). Signals received from these sensors can be directed to suitable electronic analyzing and/or computing equipment (not shown) for real-time display of information as a subject is being tested, as well as for recording of data for subsequent review and use.

The first housing 10 included within the articulating enclosure is a hollow rigid member including a recess 11 and a removable cover 12. One end of the first housing 10 is provided with a protruding hinge extension 13. The hinge extension 13 is radiused across its upper end, as can be seen in FIG. 4, and has a transverse aperture formed through it.

The lower end of second housing 14 is provided with complementary hinge extensions 20 which straddle the extension 13 of first housing 10. The extensions 20 are also radiused and transversely apertured to rotatably support a pivot shaft 21 centered along axis A—A. In the embodiment as illustrate, pivot shaft 21 is fixed to the central extension 13 of the first housing 10. A recess within the second housing 14 receives a transducer or sensor 19 connected to pivot shaft 21 for measuring relative movement between the shaft 21 and second housing 14.

The first plate 22, adapted to be strapped to the body of a subject by means of lower strap 31, is hinged to the front of the first housing 10 by a connecting pine 23. A transducer or sensor 24 within recess 11 measures relative angular movement between the pin 23 and the first housing 10.

The second plate 25, which is adapted to be secured to the body of a subject by upper strap 30, is guided along shaft 27 by a bracket 26 fixed to the plate 25. Bracket 26 and plate 25 can be physically carried on second housing 14 by any connecting arrangement that will provide the desired translation of plate 25 relative to the articulating enclosure, while imparting rotational forces to a sensor within the enclosure. As an example, the bracket 26 is illustrated in the drawings as being slidably and non-rotatably mounted to shaft 27 to accommodate extension of the spine during the motions being monitored by this device. Shaft 27 includes an axial slot 34 to which the bracket 26 is slidably keyed. The interconnection between bracket 26 and shaft 27 will thereby permit the bracket 26 and plate 25 to freely move along the length of shaft 27, but relative pivotal movement between the two plates 22 and 25 will result in pivotal movement of shaft 27 relative to the second housing 14.

The second housing 14 of the articulating enclosure rotatably supports engaged rigid shaft 27 that extends upwardly along the third axis C—C. A recess is provided within the second housing 14 for a suitable transducer or sensor 28 that measures relative movement between shaft 27 and the second housing 14.

Signals from the sensors 19, 24 and 28 can be directed to external monitoring equipment (not shown) by suitable flexible wire or cable leads extending from one or both of the housings 10, 14.

It is preferred at present to utilize analog electrical rotary potentiometers as the three sensors included within the first and second housings 10, 14. However, measurements could also be achieved by use of digital encoders and other transducers which utilize gauges, sound, electronic, magnetic or optical elements to transducer the resulting mechanical motions of the members described above to signals capable of being monitored by recorders, microprocessors or computers.

The device is designed to be attached about the lumbo-sacral joint so that the central pivotal axis of the device (line A—A) is substantially coincidental with the major flexion/extension axis of rotation of the fifth lumbar vertebra and first sacral interspace.

The first rigid plate 22 is adapted to be secured against the back of a subject at the base of the lumbar spine with the first housing 10 vertically aligned under the second housing 14 and with the first axis A—A located transversely across the first sacral interspace. This is achieved by strapping the first plate 22 distally to the superior horizontal aspect of the sacrum and by strapping the second plate 25 along the vertical axis of the lumbar spine in line with the first lumbar vertebra.

The second rigid plate 25 is adapted to be secured to the subject adjacent to the top of the lumbar spine. It has the capacity of free linear sliding motion along a supporting shaft to allow for lengthening and shortening of the lumbar spine during the measurement process. It moves along a slotted shaft so that angular rotations between the two plates 22 and 25 are transmitted along the shaft to detecting devices within the supporting articulating enclosure.

It is believed that the general manner using the described device will be evident from the drawings and above descriptions. A subject having the device strapped on his or her back, as generally illustrated in FIG. 1, can perform any desired movement without additional hindrance of stationary or supporting equipment. The portability of the instrument permits the subject to be monitored during progress of conventional work-related tasks, as well as during controlled exercise or standarized movements for mobility assessment purposes. The subject is free to move and walk about the est area, the only tether being the cable for wires leading to the device.

The device can be readily fitted upon any subject by simply adjusting the straps that mount it to the subject. Once it has been properly located on the subject's back, all further calibration can be carried out electrically on the recording or analyzing equipment utilized with the device.

Locating the device on the back of a user is relatively simple to one familiar with the anatomy of the lumbar region. It can be positioned by locating it relative to the bony anatomy of the subject or can be set at the L5 S1 vertebral interface by visual location while the subject is in a bent position. The upright shaft 27 can be visually aligned with the subject's spine, which is normally vertical. The encircling straps that frictionally hold the device to the body of the subject will accurately maintain it in place whether the subject is clothed or unclothed. The straps frictionally engage the subject's body or clothing and prevent relative movement between the plates 22 and 25 and the referenced anatomy of the subject.

The device is a fully encased apparatus. While not essential, it is desirable to produce the housings 10 and 14 from a plastic material, such as Delrin (TM), which can serve as a direct bearing for the rotatably shafts and pins included in the product.

FIGS. 5-7 show a more refined design of the invention, which is the best mode contemplated for its utilization at this point. Structural features of this embodiment that are essentially common to the embodiment of the invention illustrated in FIGS. 2-4 are identified by the same numerals as used above, and will not be described further.

In the second embodiment, the pivot shafts are isolated from the sensors by interposed gearing. As shown in FIG. 5, spur gears 35 are interposed between shaft 27 and sensor 28 within a separate recess 36. Beveled gears 37 are similarly interposed between pivot shaft 21 and sensor 19 within the second housing 14. They are located within a separate recess 38. Similarly, bevel gears 40 are provided between pin 23 and sensor 24 within a separate recess 41 formed in the first housing 10. The gears 35, 37 and 40 isolate the respective sensors from all forces other than the rotational forces monitored by them.

FIGS. 5-7 also illustrate use of outboard hollow tubes 42 pivotally mounted at each side of the first and second housings 10, 14 across the hinged joint that connects them. One end of each tube 42 is pivotally mounted within second housing 14 about an axis that is coaxial with the first axis A—A.

The tubes 42 serve two purposes. First, they are hollow and one or both of the tubes 42 can serve as a conduit for leading wires or cables from the second housing 14 to the first housing 10, or vice versa. Secondly, the tubes 42 provide outboard stabilization to the hinge axis formed by the central pivot shaft 21 that is the primary connection between the first and second housings 10, 14.

In all other respects, the two embodiments of this invention are virtually identical. Their applications and methods of use are identical.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. An apparatus for measuring angular rotations of the lumbar spine of a subject about three axes, comprising:

an articulating enclosure including first and second housings;

first pivot means joining the first and second housings for relative motion about a first axis;

first plate means operably mounted to the first housing;

the first plate means being adapted to be secured against the back of a subject at the base of the lumbar spine with the first housing vertically aligned under the second housing and with the first axis located transversely across a sacral interspace;

second plate means operably mounted to the second housing;

the second plate means being adapted to be secured to the subject adjacent tot eh tope of the lumbar spine, whereby flexion/extension of the lumbar spine will result in relative pivotal movement being imparted between the first and second housings about the first axis;

second pivot means operably mounting the first plate means to the first housing about at second axis that is perpendicular to the first axis, whereby lateral bending of the lumbar spine will result in relative pivotal motion being imparted between the first plate means and the first housing about the second axis;

third pivot means operably connecting the second plate means and second housing about a third axis perpendicular to the first and second axes, whereby axial rotation of the lumbar spine will result in relative pivotal motion being imparted between the second plate means and the second housing about the third axis; and a plurality of sensing means within the enclosure for separately measuring relative pivotal motion between the first and second housings about the first axis, between the first plate means the first housing about the second axis, and between the second plate means and the second housing about the third axis.

2. The apparatus of claim 1, wherein the first and second housings are hollow and fully enclosed, the sensing means being positioned within the two housings.

3. The apparatus of claim 1, wherein the first and second housings include integral overlapping extensions that form a hinge between them across the first axis.

4. The apparatus of claim 1 wherein the third pivot means includes an axial connection permitting free movement between the second plate and second housing along the third axis.

5. The apparatus of claim 1 wherein the third axis lies within a plane containing the second axis.

6. The apparatus of claim 1 wherein the second axis is spaced distally from the first axis.

7. An apparatus for measuring angular rotations of the lumbar spine of a subject from three axes, comprising:

an articulating enclosure including first and second housings;

a first pivot connection joining the first and second housings for relative motion about a first axis;

a first rigid plate mounted to the first housing;

the first rigid plate being adapted to be secured against the back of a subject at the base of the lumbar spine with the first housing vertically aligned under the second housing and with the first axis located transversely across a sacral interspace;

a second rigid plate mounted to the second housing;

the second rigid plate being adapted to be secured to the subject adjacent to the top of the lumbar spine, whereby flexion/extension of the lumbar spine will result in relative pivotal movement being imparted between the first and second housings about the first axis;

a second pivot connection mounting the second plate to the first housing about a second axis that is perpendicular to the first axis, whereby lateral bending of the lumbar spine will result in relative pivotal motion being imparted between the first plate and the first housing about the second axis;

a third pivot connection joining the second housing and second plate means about a third axis perpendicular to the first and second axes, whereby axial rotation of the lumbar spine will result in relative pivotal motion being imparted between the second plate and the second housing about the third axis;

the third pivot connection comprising:

a shaft rotatably mounted to the second housing and extending upwardly therefrom along the second axis; and a bracket fixed to the second plate, the bracket being slidably and non-rotatably mounted to the shaft to accommodate extension of the spine; and a plurality of sensing means within the enclosure for separately measuring relative pivotal motion between the first and second housings about the first axis, between the first plate and the first housing about the second axis, and between the second plate and the second housing about the third axis.

* * * * *